(12) United States Patent
Deguchi et al.

(10) Patent No.: US 8,551,423 B2
(45) Date of Patent: Oct. 8, 2013

(54) LIQUID SUPPLY DEVICE USING CHECK VALVE AND REACTIVE LIQUID CHROMATOGRAPHY SYSTEM

(75) Inventors: Kisaburo Deguchi, Hitachinaka (JP);
Hironori Kaji, Hitachinaka (JP);
Kimihiko Ishii, Hitachinaka (JP);
Daisuke Akieda, Hitachinaka (JP);
Kunihiko Takao, Tsuchiura (JP);
Masaru Yamasaki, Kasumigaura (JP);
Kenji Hiraku, Kasumigaura (JP);
Yoshihiro Nagaoka, Ushiku (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/386,789

(22) PCT Filed: May 26, 2010

(86) PCT No.: PCT/JP2010/003506
§ 371 (c)(1),
(2), (4) Date: Jan. 24, 2012

(87) PCT Pub. No.: WO2011/013285
PCT Pub. Date: Feb. 3, 2011

(65) Prior Publication Data
US 2012/0128533 A1      May 24, 2012

(30) Foreign Application Priority Data
Jul. 28, 2009   (JP) .................................. 2009-174881

(51) Int. Cl.
*B01L 3/02*        (2006.01)

(52) U.S. Cl.
USPC ........... 422/509; 422/500; 422/501; 422/502; 422/503; 73/61.47

(58) Field of Classification Search
USPC ................ 422/500–503, 509; 73/61.1, 61.47
See application file for complete search history.

(56) References Cited

U.S. PATENT DOCUMENTS
3,985,021 A * 10/1976 Achener et al. .............. 73/61.56

FOREIGN PATENT DOCUMENTS
| JP | 63-87564 U | 6/1988 |
| JP | 2005-273514 A | 10/2005 |
| JP | 2007-113439 A | 5/2007 |
| JP | 2008-139147 A | 6/2008 |

* cited by examiner

*Primary Examiner* — Jyoti Nagpaul
(74) *Attorney, Agent, or Firm* — Mattingly & Malur, PC (57) ABSTRACT

It is possible to correctly determine whether a change in the pressure or flow rate is caused by normal opening and closing operations of a check valve and to monitor in real time whether an operation of a check valve is normal or abnormal in a liquid supply device. Light is introduced in the check valve and a change in the quantity of light transmitted through or reflected by the check valve, caused by the opening and closing of the valve is detected, so that the opening and closing operations of the check valve can be directly detected. The check valve is arranged in a pipe in the liquid supply device, and a change in the pressure in the pipe is monitored on the basis of a signal from a pressure sensor and a signal which represents the opening and closing of the check valve.

13 Claims, 8 Drawing Sheets

FIG.8
PRIOR ART

LIQUID SUPPLY DEVICE USING CHECK VALVE AND REACTIVE LIQUID CHROMATOGRAPHY SYSTEM

BACKGROUND

The present invention relates to a reactive liquid chromatography system, and a liquid supply device used in a system for analyzing a fluid sample, such as a reactive liquid chromatography system.

In a system for analyzing a fluid sample, such as a reactive liquid chromatography system, a check valve for preventing a reverse flow of the sample is positioned preceding or following a liquid supply pump for supplying the liquid sample (see, for example, Patent Document 1 (JP-A-2005-273514)).

Figure 8:
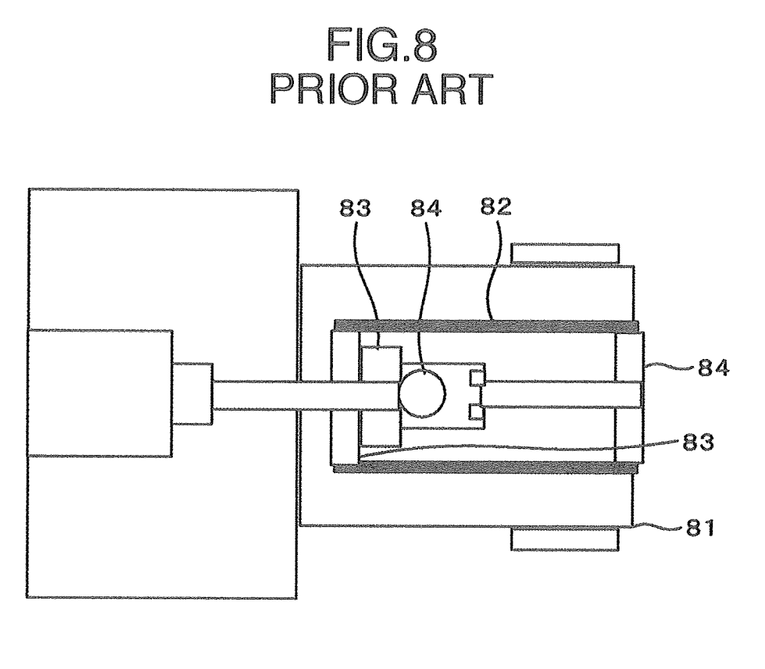
FIG. 8 illustrates a conventional example, and is a vertical cross-sectional diagram illustrating a configuration of a check valve.

FIG. 8 is a vertical cross-sectional diagram illustrating a configuration of a check valve and an example of a basic configuration of a typical check valve used in a high-pressure flow channel in a reactive liquid chromatography system or the like. The check value has a valving element that opens/closes a high-pressure flow channel inside a body of the valve depending on a slight pressure differential within the flow channel in order to prevent a reverse flow. For example, seals 83 and 84 are positioned on both ends of a check valve holder 82 housed in a stainless-steel check valve unit 81 to maintain air tightness of the body of the valve. A sapphire valve seat 83 and a ruby ball 84 are positioned inside the check valve holder 82. In the case of a flow from the left to the right in the Figure, the ruby ball 84 floats up from the sapphire valve seat 83 to open the valve. In the case of a flow from the right to the left, the ruby ball 84 is pressed against the sapphire valve seat 83 to close the valve. As described above, close contacting/floating of the ruby ball 84 with/from the sapphire valve seat 83 results in closing/opening of the check valve.

Figure 9:
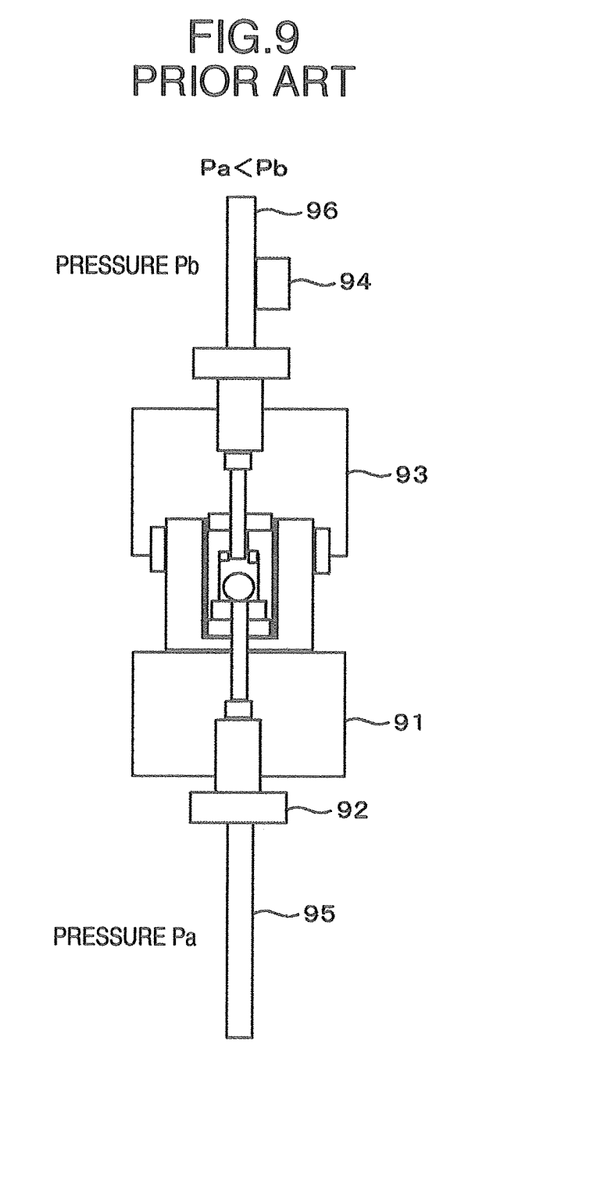
FIG. 9 illustrates a conventional example, and is a vertical cross-sectional diagram illustrating a configuration of a check valve.
Figure 10:
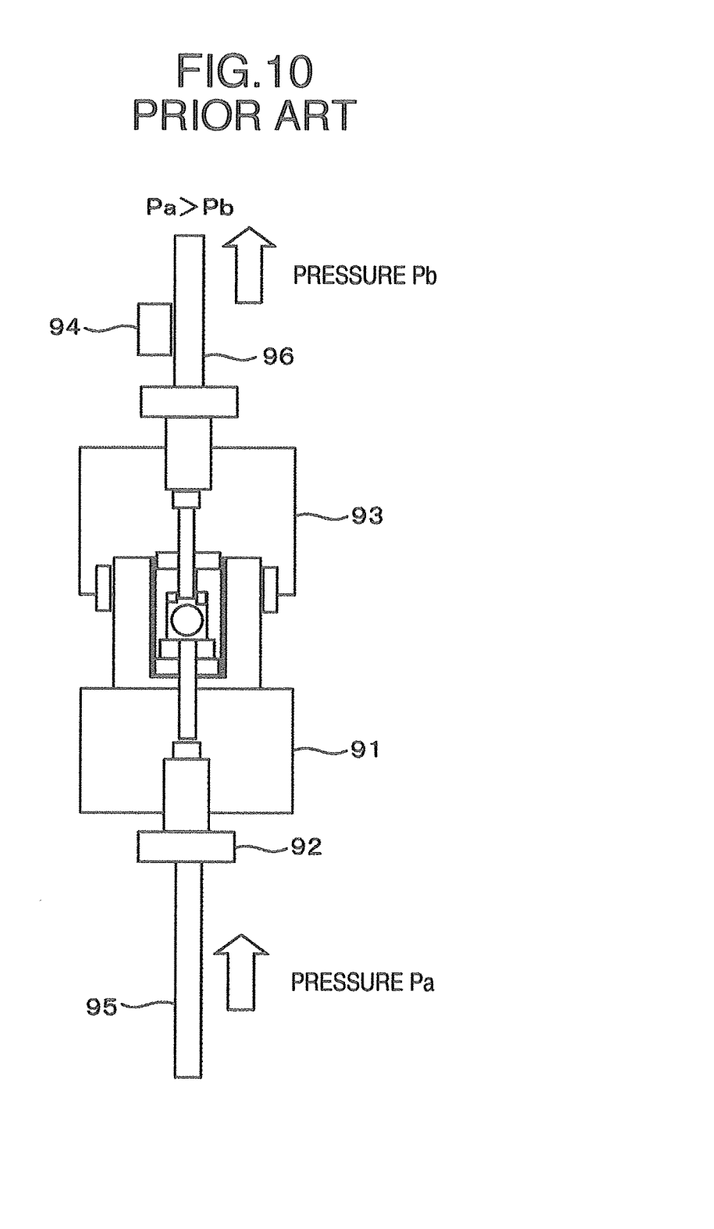
FIG. 10 illustrates a conventional example, and is a vertical cross-sectional diagram illustrating a configuration of a check valve.

FIGS. 9 and 10 are vertical cross-sectional diagrams each illustrating a configuration of a check valve and a ferrule-equipped tap bolt used for connection with a pipe. A check valve unit 91, which is illustrated in FIG. 9, is incorporated in a flow channel by an upstream-side ferrule-equipped tap bolt 92 and a downstream-side connection unit 93. A pressure sensor 94 is positioned on the downstream side of the check valve. FIG. 9 illustrates the closed valve: where a pressure Pa inside an upstream-side pipe 95 is lower than a pressure Pb inside a downstream-side pipe 96. The ruby ball 84 illustrated in FIG. 8 is brought into close contact with the sapphire valve seat 83 by a pressure differential between both these pressures.

FIG. 10 illustrates the opened valve: the pressure Pa inside the upstream-side pipe 95 is higher than the pressure Pb inside the downstream pipe 96. The ruby ball 84 illustrated in FIG. 8 floats up from the sapphire valve seat 83 by a pressure differential between both these pressures to flow a fluid. A change in pressure at this time is ordinarily monitored by the pressure sensor 94 positioned at the downstream-side pipe 96. When a flow sensor is used instead of the pressure sensor 94, a change in flow rate that increases from zero, not a change in pressure, can be monitored. As described above, a check valve is used for making a fluid flow in a single direction.

However, by means of the conventional check valves, it cannot be determined whether or not a change in pressure or flow rate is caused by, for example, normal opening/closing operation of a check valve. For example, a change in pressure or flow rate may be caused by leakage from the seals 83 and 84 of the check valve holder 82 illustrated in FIG. 8, by leakage from a sealed portion of the ferrule-equipped tap bolt 92 illustrated in FIG. 9, and by clogging of the flow channel or the like. Furthermore, there may be a case where a normal opening/closing operation of a valve cannot be performed because of sticking of the valving element in the check valve or hunting of the valve due to fluctuation in pressure of a fluid.

SUMMARY OF THE INVENTION

In order to accurately determine whether or not a change in pressure or flow rate in a pipe in a liquid supply device used in an apparatus for analyzing a fluid sample such as a reactive liquid chromatography system is caused by a malfunction of a check valve, it is necessary to directly detect and monitor opening/closing operations of the check valve.

An object of the present invention is to accurately determine whether or not a change in pressure or flow rate is caused by normal opening/closing of a check valve to monitor in real time whether the check valve operates normally or abnormally in a liquid supply device or a system therefore, and to easily perform troubleshooting for the liquid supply device and the system therefore, in order to enhance the reliability of the liquid supply device.

In order to achieve the above object, in the present invention, light is introduced to a check valve to detect a change in quantity of light passing through an the check valve or reflected by the check valve due to opening/closing of the valve to directly detect the opening/closing operation of the check valve, thereby monitoring the opening/closing. A check valve having such function is arranged at a pipe in a liquid supply device to monitor fluctuation of a pressure in the pipe depending both on a signal from a pressure sensor for detecting the pressure in the pipe and on a signal representing opening/closing of the check valve.

Embodiments of the present invention enable accurate determination of whether or not a change in pressure or flow rate is caused by normal opening/closing of a check valve to monitor in real time whether the check valve operates normally or abnormally in a liquid supply device or a system therefore, and easy troubleshooting for the liquid supply device and the system therefore to enhance the reliability of the liquid supply device.

DETAILED DESCRIPTION OF THE INVENTION

Hereinafter, embodiments of the present invention will be described with reference to the drawings. Although a liquid is contemplated for a fluid, the present invention can be applied to gases and viscous liquids.

Figure 1:
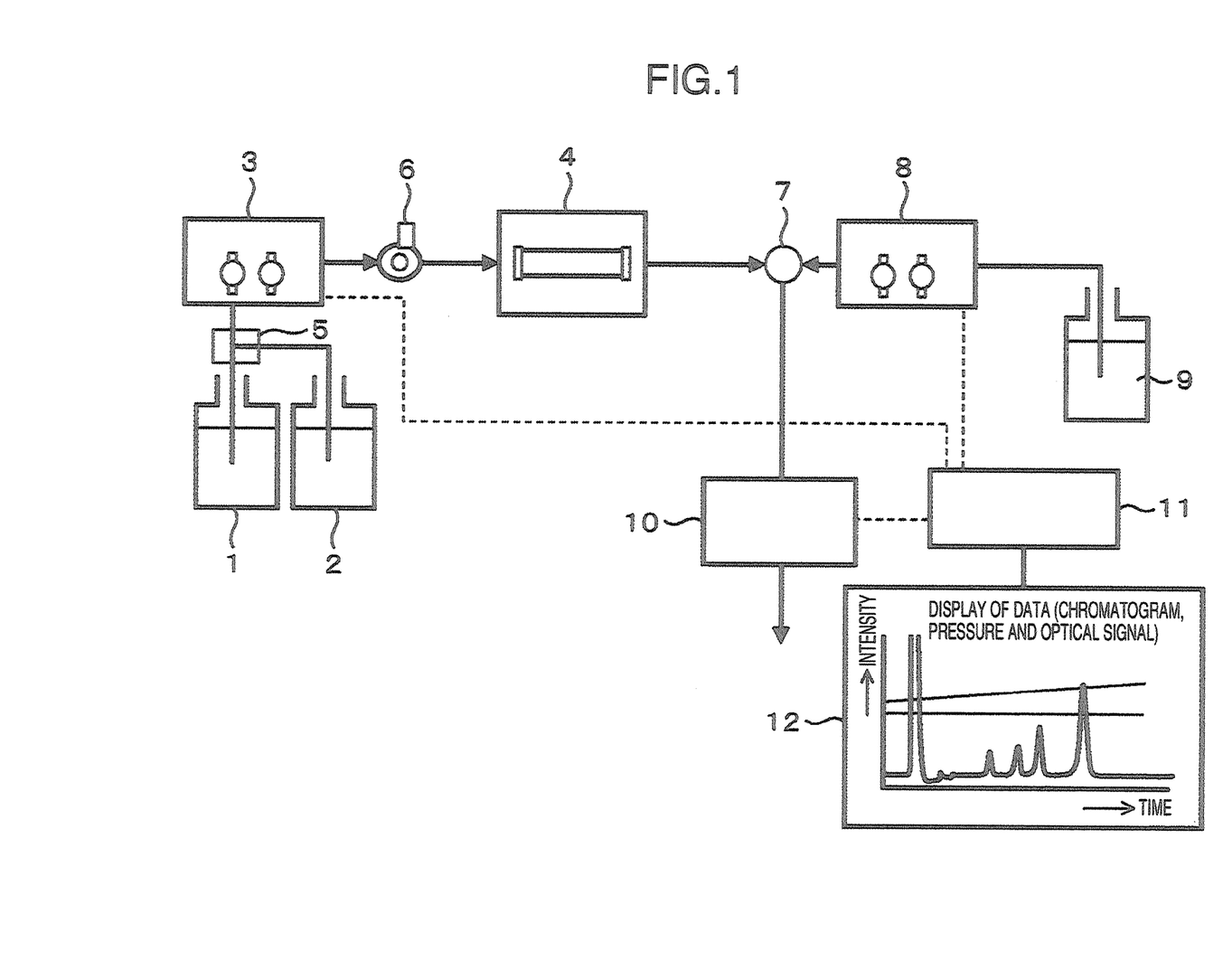
FIG. 1 is a configuration diagram illustrating a configuration of a reactive liquid chromatography system.

FIG. 1 is a configuration diagram illustrating a configuration of a reactive liquid chromatography system. In order to move a sample to be analyzed within the system, two eluents 1 and 2, which serve as carriers, are supplied to a separation column 4 by means of a separation pump 3. A mixing valve 5 mixes the two eluents 1 and 2 to produce a mixture. The sample is injected into the mixture by means of a sample injector 6 and sent to the separation column 4. In the separation column 4, while a temperature is kept constant by means of a column oven (not illustrated), the mixture is separated according to components of the sample and sent to a mixing tee 7. A reactive liquid 9 is sent to the mixing tee 7 by means of a reaction pump 8, wherein the mixture with the sample chemically reacts with the reactive liquid. A product is thus detected by a detector 10. The detected data is sent to a data processing device 11, and the data is displayed on a display 12 as illustrated in the Figure. The separation pump 3 and the reaction pump 8 send the mixture and the reactive liquid at respective predetermined flow rates. A liquid supply device according to the present invention, which employs a the separation pump 3 and the reaction pump 8, providing a non-pulsating pump for a flow with no or few pulses.

The data processing device 11 includes a data input/output unit, a processor and a memory. The device processes input data and displays the data on the display 12 in an easily viewable manner. The data includes not only chromatographic analysis data from the detector 10 but also data on a pressure of a fluid in the separation pump 3 or the reaction pump 8. These data may be displayed on the display 12 in real time, output for a print as a report, or stored in a file. Based on the real-time displayed data or the output data, inspection of operations of the separation pump 3 and/or the reaction pump 8, control for temporary halt of the pumps and processing for terminating the system involving such temporary halt, and monitoring of the operation status of the entire system and/or troubleshooting of the entire system can be performed.

Figure 2:
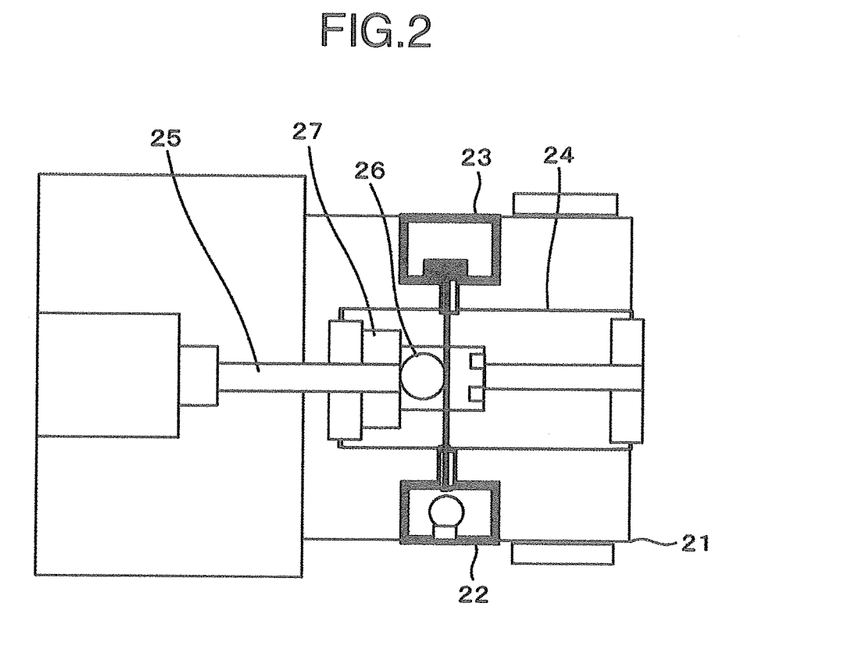
FIG. 2 is a vertical cross-sectional diagram illustrating a configuration of a check valve according to the present invention.

The separation pump 3 and the reaction pump 8 are each positioned with a check valve in order to prevent a reverse flow of a fluid. FIG. 2 is a vertical cross-sectional diagram illustrating a configuration of a check valve according to the present invention. The check valve has a structure in which a valving element that opens/closes a high-pressure flow channel by means of a slight pressure difference within the flow channel just the same as the aforementioned conventional check valve, thereby preventing a reverse flow. The check valve is different from the aforementioned conventional check valve in that a check valve unit 21 incorporates therein a light source 22 including, for example, a light-emitting diode, and a photodetector 23 including, for example, a diode detector. Furthermore, the check valve is different from the aforementioned conventional check valve in that a light transmissive material including, for example, glass is used for a check valve holder 24, in the configuration illustrated in FIG. 2. A light beam emitted from the light source section 22 is adjusted to skim over an edge portion of the ruby ball 26 when the valve is closed, that is, when an opening portion of a flow channel 25 is occluded by a ruby ball 26. Thus, a part of the light is interrupted by the ball when the valve is opened, that is, when the ruby ball 26 floats up from a sapphire valve seat 27. The quantity of light passing through the light transmissive check valve holder 24 is thus decreased. Consequently, an operation of the check valve can be monitored as a change in a light signal.

Figure 3:
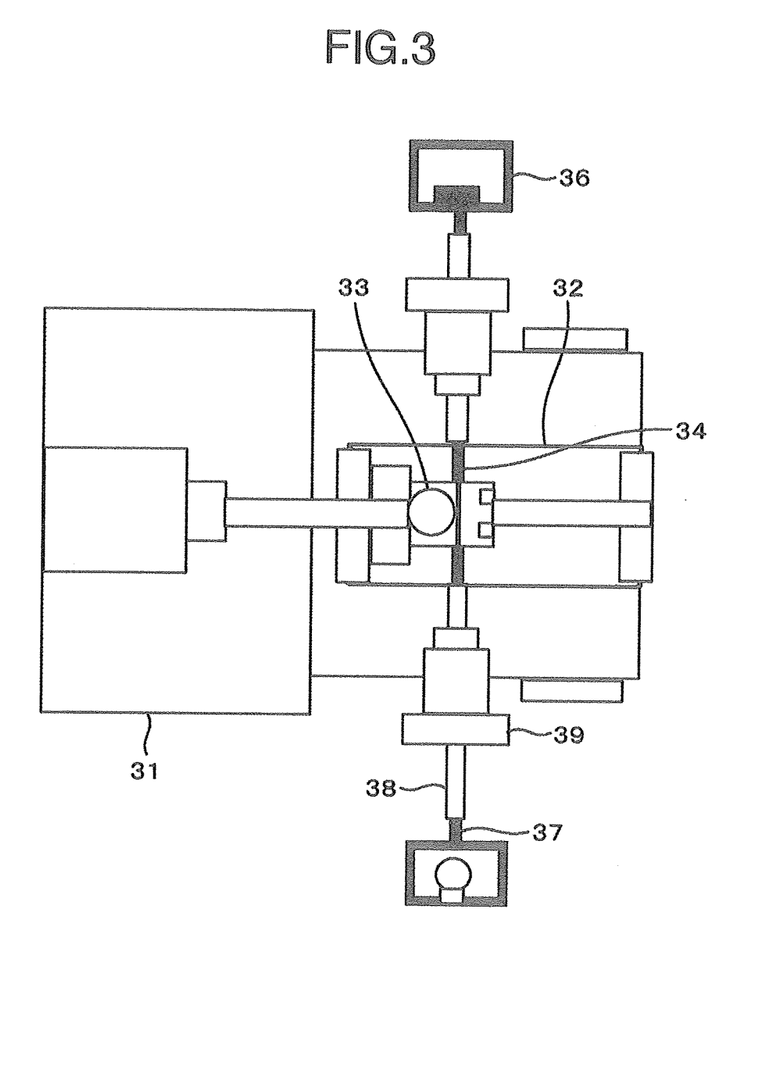
FIG. 3 is a vertical cross-sectional diagram illustrating a configuration of a high-pressure resistance check valve according to the present invention.

FIG. 3 is a vertical cross-sectional diagram illustrating a configuration of a high-pressure resistance check valve according to the present invention. Since a fluid flowing inside the valve is under high pressure, a check valve unit 31 as well as a check valve holder 32 are typically made of a metal such as a stainless steel. In order to make light pass through the check valve holder 32 for detecting a position of a ruby ball 33, an orifice 34 is formed and a light source section 35 and a photodetector 36 are configured as follows.

An optical fiber 37 for guiding light from the light source section 35 is covered by a sleeve 38 and sealed with a ferrule-equipped tap bolt 39, which is used for a reactive liquid chromatograph. The photodetector 36 is configured in a similar manner to the above. The optical fiber 37 eliminates the need to embed the light source 35 and the photodetector 36 in a body of the check valve. Thus, the check valve can have a high-pressure resistance. The light source section 35 and the photodetection section 36 can also be positioned at an arbitrary position away from the check valve, providing the advantageous effect for easier arrangement of the device.

Although the check valves illustrated in FIGS. 2 and 3 each employ a combination of a ruby ball and a sapphire valve seat as an example, a structure for detecting opening/closing of the valve by means of light according to the present invention can easily be employed for a combination of a stainless-steel ball and a stainless-steel valve seat or a configuration using a valving film instead of a ball.

Figure 4:
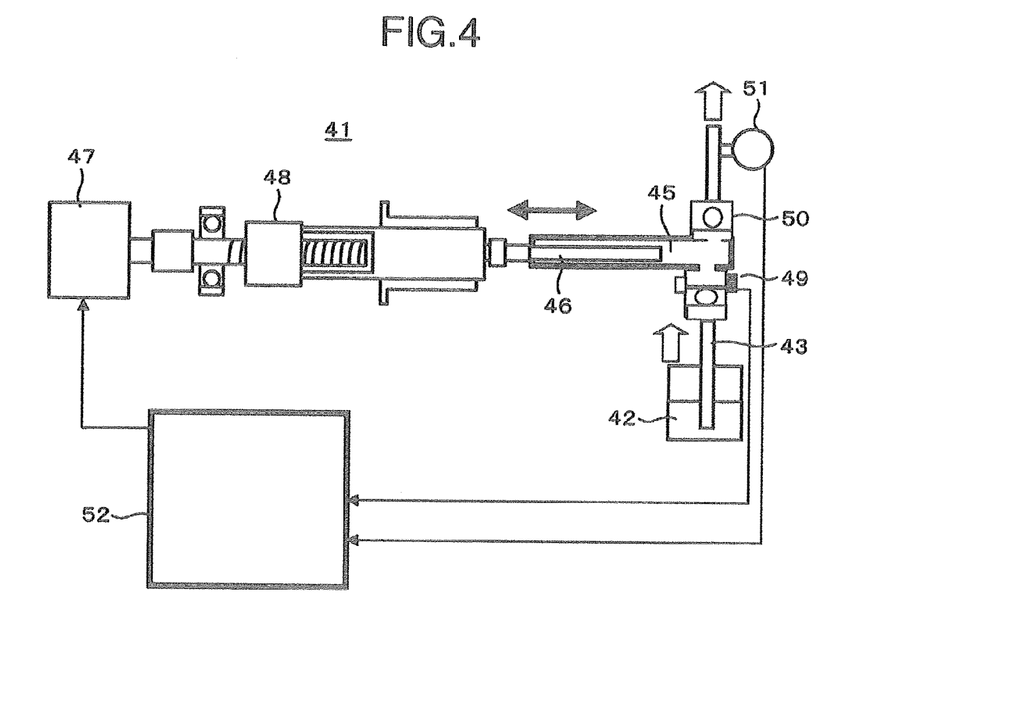
FIG. 4 is a vertical cross-sectional diagram illustrating a schematic configuration of a liquid supply pump with a photodetection function-provided check valve incorporated therein.

FIG. 4 is a vertical cross-sectional diagram illustrating a schematic configuration of a liquid supply pump that incorporates therein a photodetection function-provided check valve such as illustrated in FIGS. 2 and 3. A liquid supply pump 41 is intended to send a solution 42 from a pipe 43 to a pipe 44. In order to reciprocate a plunger 46 in a cylinder 45 in which a main mechanism of the liquid supply pump 41 is incorporated, rotation of a shaft of a motor 47 is converted to reciprocating motion by means of a ball screw 48. A check valve 49 is positioned on the side of the cylinder 45 from which a solution 42 is sucked, and a check valve 50 is positioned on the side of the cylinder 45 from which the solution 42 is discharged. FIG. 4 illustrates an example in which a photodetection function-provided check valve such as illustrated in FIG. 2 or 3 is positioned on the suction side. A signal indicating opening/closing of the valve in the check valve 49, and a signal from a pressure sensor 51 detecting a pressure of the solution 42 compressed by the liquid supply pump 41 are sent to a motor controller 52. The motor controller 52 determines whether or not a change in pressure or flow rate of the solution in the pipe is caused by a malfunction of the check valve, and controls a motor 47 for the liquid supply pump 41.

Although the example of the liquid supply pump 41 in the Figure indicates a pump to reciprocate the plunger 46 by the ball screw 48, a pump for moving the plunger 46 by a cam is commonly used. In this case, also, a photodetection function-provided check valve can be used. A photodetection function-provided check valve can be used in a one push-type pump.

Figure 5:
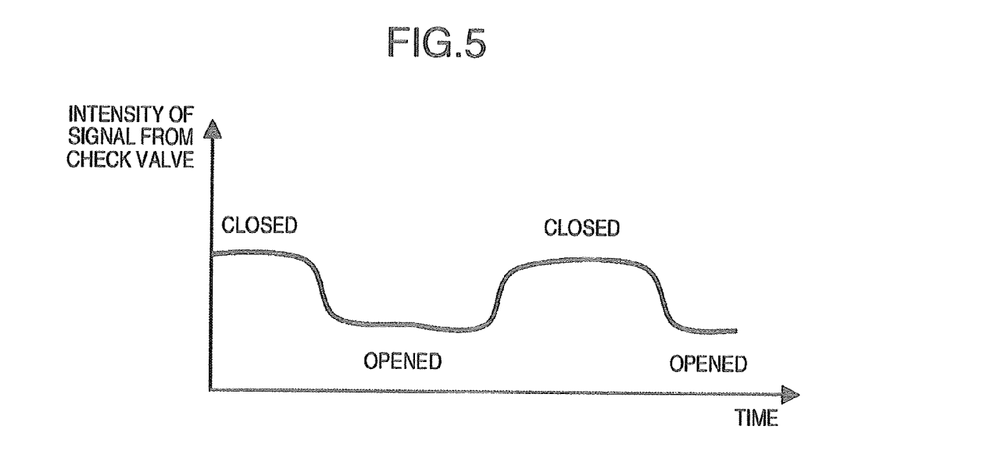
FIG. 5 is a graph illustrating temporal change in intensity of a signal from a check valve.
Figure 6:
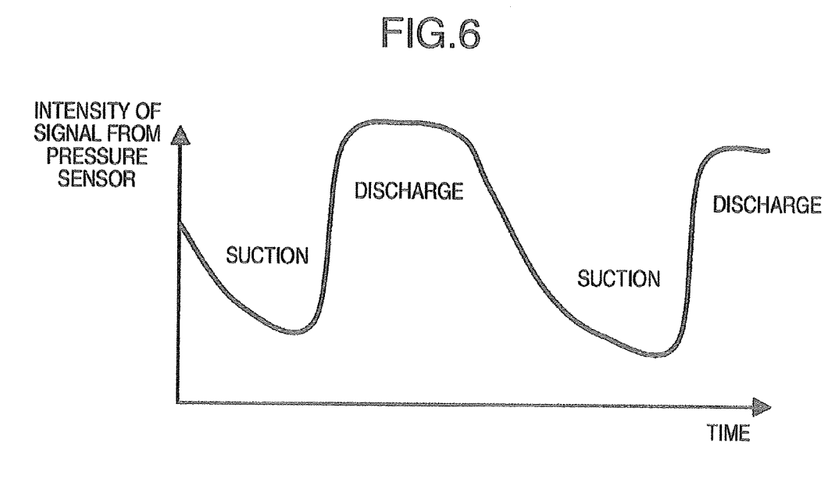
FIG. 6 is a graph illustrating temporal change in intensity of a signal from a pressure sensor.

FIG. 5 is a graph indicating temporal change in intensity of a signal from a photodetection function-provided check valve, and indicates a case where a photodetection function-provided check valve is positioned on the discharge side. FIG. 6 is a graph indicating temporal change in intensity of a signal from the pressure sensor 51.

While the liquid supply pump 41 is sending a solution, the ruby ball 26 illustrated in FIG. 2 in the discharge-side photodetection function-provided check valve 50 floats up from the sapphire valve seat 27, whereby the valve is opened, and thus, the intensity of the signal decreases. The pressure in that time is low. While the pump is sucking the solution 42 or compressing the solution 42 for preliminary compression, the valve in the discharge-side check valve 50 is closed, and the intensity of the signal thus increases. Furthermore, when a pressure inside the cylinder 45 exceeds a pressure inside the discharge-side check valve 50, the pump resumes sending the solution. The pressure thus starts increasing. In each cycle of a pumping operation, the cycle of the intensity of the signal from the check valve 50 corresponds to the cycle of the intensity of the signal from the pressure sensor 51.

When an abnormality is observed in the intensity of the signal from the pressure sensor 51, if an abnormality is also observed in the intensity of the signal from the check valve 50, it can easily be determined that such abnormality is caused by a malfunction of the check valve 50. If the intensity of the signal from the check valve 50 is normal, there may be a cause other than a malfunction of the check valve 50. The cause may be, for example, liquid leakage, clogging or a malfunction of the suction-side check valve 49. As described above, the intensity of the signal from the check valve is monitored and stored as data in real time to facilitate inspecting the operation of the pump and troubleshooting the pump.

In the example illustrated in FIGS. 5 and 6, the speed of the plunger 46 illustrated in FIG. 4 is constant in suction and discharge steps of the pump. However, in order to minimize the pressure loss in the suction steps, the time of suction steps and the preliminary compression steps, that is, the time when the photodetection function-provided check valve 50 is closed is shortened as possible. That is, the motor 47 can be controlled so that the speed of the plunger 46 in these steps is, for example, twice or three times as fast as that of the discharge steps. This is called quick-return control. In this case, it is important to determine an end point of a preliminary compression step. The pressure signal from the pressure sensor 51 sharply rises after the end point and overshoots. After the motor controller 52 detects such pressure rise, the motor controller 52 make the speed of the motor 47 returned to its original speed.

Quick-return control such as described above can also be performed by using the intensity of the signal from the photodetection function-provided check valve. In other words, before an end point of a preliminary compression step, the pressure inside the cylinder 45 in the liquid supply pump 41 is lower than a pressure outside the pump, but becomes equal to the pressure outside the pump at the end point, and subsequently becomes higher than the pressure outside the pump. The ruby ball 26 in the photodetection function-provided check valve moves and floats up from the sapphire valve seat 27, changing the intensity of the signal. The speed of the motor 47 is returned to its original speed at a time point when the photodetection function-provided check valve is opened. That is, the time point is defined as the end point of the preliminary compression step. The pressure gradually rises in this method, preventing overshooting due to a sharp pressure rise.

Figure 7:
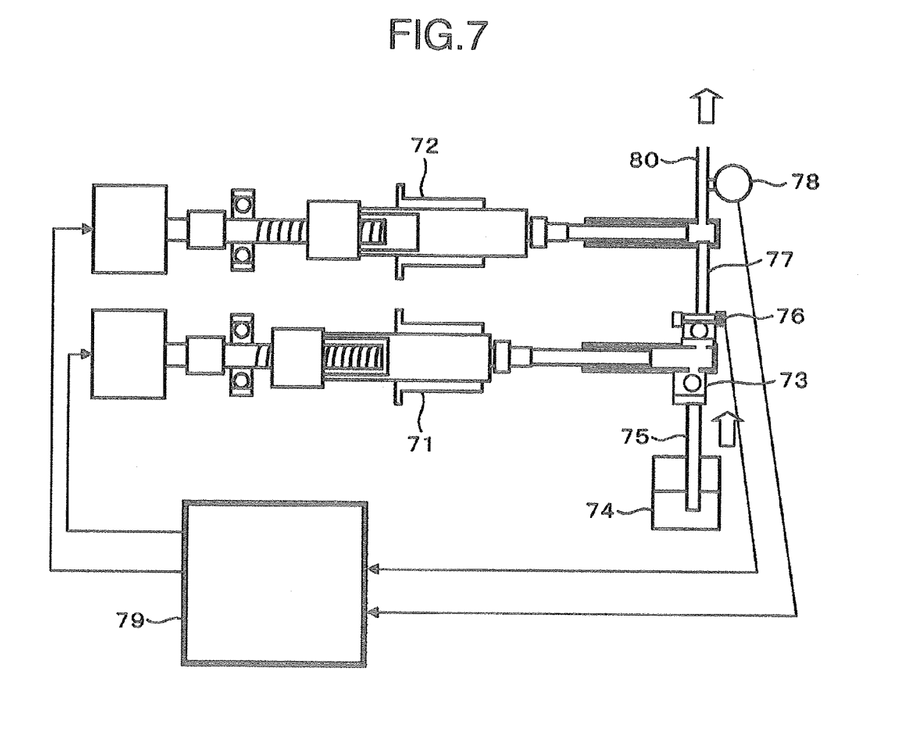
FIG. 7 is a vertical cross-sectional diagram illustrating a configuration of a liquid supply device.

FIG. 7 is a vertical cross-sectional diagram illustrating a liquid supply device in which another liquid supply pump is arranged in series to the liquid supply pump in addition to the liquid supply pump illustrated in FIG. 4 to send a solution. In this serial arrangement, the upstream-side pump is referred to as a first pump 71, and the downstream-side pump is referred to as a second pump 72. A suction-side check valve 73 is arranged between a pipe 75 on the solution 74 side and the first pump 71. A discharge-side check valve 76 is arranged between the first pump 71 and the second pump 72. For example, FIG. 7 illustrates an example in which the discharge-side check valve 76 is mounted on a part between the first pump 71 and a pipe 77. In the example in FIG. 7, a photodetection function-provided check valve is used for the discharge-side check valve 76. However, a photodetection function-provided check valve may be used for the suction-side check valve, or may be used for both of them. A signal from the discharge-side check valve 76 and a signal from a pressure sensor 78 are sent to a motor controller 79. The motor controller 79 controls a motor for the first pump 71 and a motor for the second pump 72 respectively.

In the example in FIG. 7, the first pump 71 sucks and compresses the solution 74, and sends the solution 74 from a pipe 80 via the second pump 72. The second pump 72 discharges the solution 74 that has been compressed by the first pump 71 when the first pump 71 cannot send the solution 74 during suction and subsequent preliminary compression steps. At a point of time when the first pump 71 finished the preliminary compression step and starts a discharge step, the second pump 72 sucks a part, for example, half of the compressed solution 74 for preparation for a next discharge. Such cooperative operations of the first pump 71 and the second pump 72 provide liquid supply with a constant flow rate and fewer flow pulses. Since the liquid supply pumps illustrated in FIG. 7 have a variable stroke length, each stroke lengths of the first pump 71 and the second pump 72 can be adjusted independently, providing liquid supply with a constant flow rate and fewer flow pulses.

In addition to the liquid supply pump illustrated in FIG. 7, a serial or parallel combination of cam-driven pumps can be employed to achieve similar effect by using photodetection function-provided check valve(s). However, where plungers in first and second pumps are actuated by means of one motor using a cam method, it should be noted that the phases of operations of the first and second pumps are fixed each other.

It is a subject for the liquid supply pump illustrated in FIG. 7 to detect an end of a preliminary compression step and to control a motor for the first pump and a motor for the second pump. For example, JP-A-4-234578 describes that motors are controlled so as to minimize pressure ripples at an end point of a preliminary compression step (corresponding to fluctuation in the signal from the pressure sensor 78 in FIG. 7). For example, JP-A-7-072130 and WO2003/0079000 described that an additional pressure sensor is attached to a head of a cylinder of a first pump and that motors are controlled based on a point of time when a value of the pressure sensor corresponds to a value of the pressure sensor 78. That is, the point of time is defined as an end point of a preliminary compression step.

In the embodiment of the present invention illustrated in FIG. 7, the signal from the photodetection function-provided discharge-side check valve 76 is used, wherein the signal indicating opening/closing of the valve is opened/closed. Before an end point of a preliminary compression step, the pressure inside the cylinder of the first pump 71 is lower than the pressure inside the cylinder of the second pump 72, but becomes equal to the pressure inside the cylinder of the second pump 72 at the end point and subsequently becomes higher than the pressure inside the cylinder of the second pump 72. The ruby ball 26 illustrated in FIG. 2 inside the photodetection function-provided check valve 76 moves and floats up from the sapphire valve seat 27, changing the intensity of the signal. A timing for opening/closing the valve in the photodetection function-provided discharge-side check valve 76 is thus determined accurately. Furthermore, the change in the intensity of the signal for the photodetection function-provided discharge-side check valve 76 can be displayed in real time on a display or stored as data, providing the advantageous effect of facilitating an inspection of operation of the pump and troubleshooting.

As described above, the embodiments of the present invention can solve problems of conventional check valves such as it being unable to correctly determine whether or not a change in pressure or flow rate is caused by normal opening/closing of a check valve. In other words, a liquid supply device incorporating a photodetection function-provided check valve according to the present invention therein can distinguish between a change in pressure or flow rate caused by liquid leakage from a connection part or sealed part of a flow channel system, clogging of a flow channel or the like, and a change in pressure or flow rate caused by a malfunction of the check valve. It become possible to monitor in real time whether or not a check valve normally operates in a liquid supply device and a system therefore. It also becomes possible to facilitate troubleshooting of the liquid supply device and the system therefore to enhance the reliability of the liquid supply device.

REFERENCE SIGNS LIST 1, 2 eluent
3 separation pump
4 separation column
5 mixing valve
6 sample injector
7 mixing tee
8 reaction pump
9 reactive liquid
10 detector
11 data processing device
12 display
21, 31 check valve unit
22, 35 light source section
23, 36 photodetector
24, 32 check valve holder
26, 33 ruby ball
27 sapphire valve seat
41 liquid supply pump
45 cylinder
46 plunger
47 motor
49, 50 check valve
51, 78 pressure sensor
52, 79 motor controller
71 first pump
72 second pump
73 suction-side check valve
76 discharge-side check valve

The invention claimed is:

1. A liquid supply device using a check valve, comprising:
a pump sucking a sample from a pipe and discharging the sample;
a pressure sensor detecting a pressure in a pipe on the downstream side of the pump;
a control device controlling the pump depending on a pressure detected by the pressure sensor;
a first check valve positioned on the suction side of the pump; and
a second check valve positioned on the discharge side of the pump,
wherein at least one of the first check valve and the second check valve includes a ruby ball occluding an opening of a flow channel, a sapphire valve seat contacting with the ruby ball to occlude the opening, a light source applying light to a part of the ruby ball, and a photodetector detecting the light from the light source, and
wherein the control device controls the pump based on determining whether or not a change in pressure and/or flow rate of the solution in the pipe is caused by a malfunction of the at least one check valve depending on a correlation between a signal for opening/closing of the at least one check valve from the photodetector and the pressure detected by the pressure sensor in each cycle of a pumping operation.

2. The device according to claim 1, wherein a part of the at least one check valve includes a transparent or semitransparent member to allow the light from the light source to pass therethrough.

3. The device according to claim 1, wherein the light from the light source is guided to a body of the at least one check valve via an optical fiber.

4. The device according to claim 1, wherein the photodetector detects the light guided to a body of the at least one check valve via an optical fiber.

5. The device according to claim 1, wherein a plurality of the pumps are arranged, and the first check valve is positioned on the suction side of a first pump on upstream side, and the second check valve is positioned on the discharge side of the first pump.

6. The device according to claim 5, wherein the pressure sensor is positioned at a pipe on the discharge side of a downstream-side pump among the plurality of the pumps.

7. The device according to claim 1, wherein, when an abnormality is observed in the intensity of the signal detected by the pressure sensor, if an abnormality is also observed in the intensity of the signal for opening/closing of the at least one check valve from the photodetector, the control device determines that the change in pressure and/or flow rate of the solution in the pipe is caused by the malfunction of the check valve.

8. A reactive liquid chromatography system, comprising:
a separation pump sending two eluents served as carriers for a sample to be analyzed to a mixing tee via a separation column;
an injector injecting the sample into a pipe between the separation pump and the separation column;
the separation column separating the eluents containing the sample;
a reaction pump sending a reactive liquid to the mixing tee via a different pipe from the pipe for the eluents;
a detector detecting a product produced as a result of a chemical reaction between the eluents containing the sample and the reactive liquid;
a data processing device for analyzing the product detected by the detector and generating data;
a first check valve positioned on the suction side of at least one of the separation pump and the reaction pump;
a second check valve positioned on the discharge side of the pump;
a pressure sensor detecting a pressure in a pipe on the downstream side of the pump; and
a control device controlling the pump depending on a pressure detected by the pressure sensor;
wherein at least one of the first check valve and the second check valve includes a ruby ball occluding an opening of a flow channel, a sapphire valve seat contacting with the ruby ball to occlude the opening, a light source applying light to a part of the ruby ball, and a photodetector detecting the light from the light source, and wherein the control device controls the pump depending both on a signal for opening/closing of the check valve from the photodetector and on the pressure detected by the pressure sensor.

9. The system according to claim 8, wherein a part of the check valve includes a transparent or semitransparent member to allow the light from the light source to pass therethrough.

10. The system according to claim 8, wherein the light from the light source is guided to a body of the check valve via an optical fiber.

11. The system according to claim 8, wherein the photodetector detects the light guided from a body of the check valve via an optical fiber.

12. The system according to claim 8, wherein a plurality of the pumps are arranged, and the first check valve is positioned on the suction side of a first pump on upstream side, and the second check valve is positioned on the discharge side of the first pump.

13. The system according to claim 12, wherein the pressure sensor is positioned at a pipe on the discharge side of a downstream-side pump among the plurality of the pumps.

* * * * *